United States Patent
Hanbury

(10) Patent No.: US 12,076,496 B2
(45) Date of Patent: *Sep. 3, 2024

(54) NON-PHARMACEUTICAL SYSTEMS AND METHODS OF TREATING THE SYMPTOMS OF FIBROMYALGIA

(71) Applicant: Sana Health, Inc., Louisville, CO (US)

(72) Inventor: Richard Hanbury, Lafayette, CO (US)

(73) Assignee: SANA HEALTH, INC., Louisville, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/079,443

(22) Filed: Dec. 12, 2022

(65) Prior Publication Data

US 2023/0106753 A1    Apr. 6, 2023

Related U.S. Application Data

(63) Continuation of application No. 16/925,031, filed on Jul. 9, 2020, now Pat. No. 11,524,135.

(60) Provisional application No. 62/872,577, filed on Jul. 10, 2019.

(51) Int. Cl.
*A61M 21/02* (2006.01)
*A61M 21/00* (2006.01)

(52) U.S. Cl.
CPC ..... *A61M 21/02* (2013.01); *A61M 2021/0022* (2013.01); *A61M 2021/0027* (2013.01); *A61M 2021/0044* (2013.01); *A61M 2230/06* (2013.01); *A61M 2230/08* (2013.01); *A61M 2230/10* (2013.01); *A61M 2230/50* (2013.01); *A61M 2230/63* (2013.01); *A61M 2230/65* (2013.01)

(58) Field of Classification Search
CPC .......... A61M 21/02; A61M 2021/0022; A61M 2021/0027; A61M 2021/0044; A61M 2230/06; A61M 2230/08; A61M 2230/10; A61M 2230/50; A61M 2230/63; A61M 2230/65; A61M 2230/04; A61M 2230/205; A61M 2230/60
USPC ..................................................... 600/26–28
See application file for complete search history.

(56) References Cited

U.S. PATENT DOCUMENTS

| 2006/0106276 A1* | 5/2006 | Shealy ............. | A61M 21/00 600/27 |
| 2011/0257712 A1* | 10/2011 | Wells ............... | A61B 5/6886 607/90 |
| 2013/0190556 A1* | 7/2013 | Wetmore .......... | A61M 21/00 600/27 |
| 2017/0312476 A1* | 11/2017 | Woo ................. | A61M 21/02 |

(Continued)

FOREIGN PATENT DOCUMENTS

WO    WO-2015028480 A1 *  3/2015  ............. H04R 25/75

OTHER PUBLICATIONS

M. Hulens et al., Fibromyalgia and unexplained widespread pain: The idiopathic cerebrospinal pressure dysregulation hypothesis, Medical Hypotheses, vol. 110, 2018, pp. 150-154, ISSN 0306-9877, https://doi.org/10.1016/j.mehy.20 (Year: 2018).*

*Primary Examiner* — Sunita Reddy
(74) *Attorney, Agent, or Firm* — Dickinson Wright PLLC; Charles W. Kocher, II

(57) ABSTRACT

Non-pharmaceutical systems and methods of treating the symptoms of fibromyalgia are described. The method includes administering a therapeutically effective amount of a sensory stimulus to a person, wherein the sensory stimulus includes one or more visual stimuli and one or more auditory stimuli.

13 Claims, 8 Drawing Sheets

(56) References Cited

U.S. PATENT DOCUMENTS

2018/0050170 A1\* 2/2018 Kuhl ...................... G16H 20/70
2018/0318545 A1\* 11/2018 Jones .................... A61M 21/02
2019/0070057 A1\* 3/2019 Conner ................. A61H 23/02
2020/0376230 A1\* 12/2020 Causey ................. A61M 21/02
2021/0213239 A1\* 7/2021 Jones .................... A61M 21/02

\* cited by examiner

| Segments A1-A4 for 120s | Auditory Left | Auditory Right | Light Left | Light Right |
|---|---|---|---|---|
| Segment A1 (Light and Auditory both sides pulse together) Repeat 116 times, followed by 0.5 sec gap | On 0.1277 sec | On 0.1277 sec | On 0.1277 sec | On 0.1277 sec |
| | Off 0.1277 sec | Off 0.1277 sec | Off 0.1277 sec | Off 0.1277 sec |
| Segment A2 (light and auditory on left side, alternating light and auditory on right). Repeat 116 times, followed by 0.5 sec gap | On 0.1277 sec | Off 0.1277 sec | On 0.1277 sec | Off 0.1277 sec |
| | Off 0.1277 sec | On 0.1277 sec | Off 0.1277 sec | On 0.1277 sec |
| Segment A3 (both lights together, alternating with both auditory signals together) Repeat 115 times, followed by 0.5 sec gap | On 0.1277 sec | On 0.1277 sec | Off 0.1277 sec | Off 0.1277 sec |
| | Off 0.1277 sec | Off 0.1277 sec | On 0.1277 sec | On 0.1277 sec |
| Segment A4 (auditory left and light right together, alternating auditory right and light left together) Repeat 115 times, followed by 0.5 sec gap | On 0.1277 sec | Off 0.1277 sec | Off 0.1277 sec | On 0.1277 sec |
| | Off 0.1277 sec | On 0.1277 sec | On 0.1277 sec | Off 0.1277 sec |

FIG. 5

| Segments B1-B4 for 120s | Auditory Left | Auditory Right | Light Left | Light Right |
|---|---|---|---|---|
| Segment B1 (Light and Auditory both sides pulse together) Repeat 45 times, followed by 0.5 sec gap | On 0.3333 sec | On 0.3333 sec | On 0.3333 sec | On 0.3333 sec |
| | Off 0.3333 sec | Off 0.3333 sec | Off 0.3333 sec | Off 0.3333 sec |
| Segment B2 (light and auditory on left side, alternating light and auditory on right) Repeat 44 times, followed by 0.5 sec gap | On 0.3333 sec | Off 0.3333 sec | On 0.3333 sec | Off 0.3333 sec |
| | Off 0.3333 sec | On 0.3333 sec | Off 0.3333 sec | On 0.3333 sec |
| Segment B3 (both lights together, alternating with both auditory signals together) Repeat 44 times, followed by 0.5 sec gap | On 0.3333 sec | On 0.3333 sec | Off 0.3333 sec | Off 0.3333 sec |
| | Off 0.3333 sec | Off 0.3333 sec | On 0.3333 sec | On 0.3333 sec |
| Segment B4 (auditory left and light right together, alternating auditory right and light left together) Repeat 44 times, followed by 0.5 sec gap | On 0.3333 sec | Off 0.3333 sec | Off 0.3333 sec | On 0.3333 sec |
| | Off 0.3333 sec | On 0.3333 sec | On 0.3333 sec | Off 0.3333 sec |

| Repeat the following Segments C1-C4 6 times for a total of 12 minutes | Auditory Left | Auditory Right | Light Left | Light Right |
|---|---|---|---|---|
| Segment C1 (Light and Auditory both sides pulse together) Repeat 15 times, followed by 1 sec gap | On 1 sec | On 1 sec | On 1 sec | On 1 sec |
| | Off 1 sec | Off 1 sec | Off 1 sec | Off 1 sec |
| Segment C2 (light and auditory on left side, alternating light and auditory on Right) Repeat 15 times, followed by 1 sec gap | On 1 sec | Off 1 sec | On 1 sec | Off 1 sec |
| | Off 1 sec | On 1 sec | Off 1 sec | On 1 sec |
| Segment C3 (both lights together, alternating with both auditory signals together) Repeat 14 times, followed by 1 sec gap | On 1 sec | On 1 sec | Off 1 sec | Off 1 sec |
| | Off 1 sec | Off 1 sec | On 1 sec | On 1 sec |
| Segment C4 (auditory left and light right together, alternating auditory right and light left together) Repeat 14 times, followed by 1 sec gap | On 1 sec | Off 1 sec | Off 1 sec | On 1 sec |
| | Off 1 sec | On 1 sec | On 1 sec | Off 1 sec |

FIG. 7

NON-PHARMACEUTICAL SYSTEMS AND METHODS OF TREATING THE SYMPTOMS OF FIBROMYALGIA

CROSS-REFERENCE TO RELATED APPLICATIONS

This patent application is a continuation of U.S. application Ser. No. 16/925,031 filed Jul. 9, 2020, titled "Non-Pharmaceutical Systems and Methods of Treating the Symptoms of Fibromyalgia," which claims priority to U.S. Provisional Patent Application Ser. No. 62/872,577, filed on Jul. 10, 2019, the entire disclosures of the aforementioned patent applications are incorporated herein by reference.

BACKGROUND

Field of the Disclosure

This disclosure generally relates to treating people suffering from fibromyalgia, and more particularly to a non-pharmaceutical method of treating the symptoms of fibromyalgia.

Discussion of the Background

Fibromyalgia is a medical condition characterized by chronic widespread pain and a heightened pain response to pressure. Other symptoms include tiredness to a degree that normal activities are affected, sleep problems and troubles with memory. Some people also report restless legs syndrome, bowel or bladder problems, numbness and tingling and sensitivity to noise, lights or temperature. Fibromyalgia is frequently associated with depression, anxiety, and post-traumatic stress disorder. Other types of chronic pain are also frequently present.

The cause of fibromyalgia is unknown; however, it is believed to involve a combination of genetic and environmental factors, with each playing a substantial role. The condition runs in families and many genes are believed to be involved. Environmental factors may include psychological stress, trauma and certain infections. The pain appears to result from processes in the central nervous system and the condition is referred to as a "central sensitization syndrome." Fibromyalgia is recognized as a disorder by the US National Institutes of Health and the American College of Rheumatology.

The treatment of fibromyalgia can be difficult. Recommendations often include getting enough sleep, exercising regularly, and eating a healthy diet. Cognitive behavioral therapy (CBT) may also be helpful. The medications duloxetine, milnacipran, or pregabalin may be used. Use of opioid pain medication is controversial, with some stating their usefulness is poorly supported by evidence and others saying that weak opioids may be reasonable if other medications are not effective. Dietary supplements lack evidence to support their use. While fibromyalgia can last a long time, it does not result in death or tissue damage.

Fibromyalgia is estimated to affect 2-8% of the population. Women are affected about twice as often as men. Rates appear similar in different areas of the world and among different cultures. (Wikipedia contributors. "Fibromyalgia." *Wikipedia, The Free Encyclopedia*. Wikipedia, The Free Encyclopedia, 26 Jun. 2019. Web. 2 Jul. 2019).

Thus, there is a need for tools and methods for treating the symptoms of fibromyalgia.

SUMMARY

The present disclosure overcomes the disadvantages of the prior art by providing a nonpharmaceutical method of treating symptoms of fibromyalgia.

It is one aspect of certain embodiments to provide a method of treating fibromyalgia. The method includes administering a therapeutically effective amount of a sensory stimulus to a person, wherein the sensory stimulus includes one or more visual stimuli and one or more auditory stimuli.

It is another aspect to provide a system for treating fibromyalgia. The system includes a headset configured to be worn on a head of a person; wherein the headset is configured to administer a therapeutically effective amount of a sensory stimulus to the person; and wherein the sensory stimulus includes one or more visual stimuli and one or more auditory stimuli.

It is another aspect to provide a method to treat one or more symptoms of fibromyalgia, where the symptoms may include one or more of anxiety, pain, depression, and lack of quality of sleep.

It is yet another aspect to provide a method of treating fibromyalgia. The method includes providing a headset to be worn by the person; and administering, with the headset, the therapeutically effective amount of a sensory stimulus to the person.

In certain embodiments sensory stimulus is provided to a person using devices and methods described in U.S. patent application Ser. No. 15/360,808 (the '808 patent application) and in U.S. patent application Ser. No. 15/910,252 (the '252 patent application). The '808 and '252 patent applications are co-owned with the present patent application and are both herein included by way of incorporation in their entirety.

These features together with the various ancillary provisions and features which will become apparent to those skilled in the art from the following detailed description are attained by the method of the present disclosure, preferred embodiments thereof being shown with reference to the accompanying drawings, by way of example only, wherein:

BRIEF DESCRIPTION OF THE DRAWINGS

For a more complete understanding of this disclosure and its advantages, reference is now made to the following description, taken in conjunction with the accompanying drawings. It is emphasized that, according to common practice, the various features of the drawings are not to-scale. On the contrary, the dimensions of the various features are arbitrarily expanded or reduced for clarity.

FIGS. 5, 6, and 7 generally illustrate tables showing several treatment stimulus segments of FIG. 4 according to principles of the present disclosure.

Reference symbols are used in the Figures to indicate certain components, aspects or features shown therein, with reference symbols common to more than one Figure indicating like components, aspects or features shown therein.

DETAILED DESCRIPTION

The following discussion is directed to various embodiments of the present disclosure. Although one or more of these embodiments may be preferred, the embodiments disclosed should not be interpreted, or otherwise used, as limiting the scope of the disclosure, including the claims. In addition, one skilled in the art will understand that the following description has broad application, and the discussion of any embodiment is meant only to be exemplary of that embodiment, and not intended to intimate that the scope of the disclosure, including the claims, is limited to that embodiment.

Various embodiments described herein are directed to non-pharmaceutical methods of treating fibromyalgia. The methods include administering a therapeutically effective amount of a sensory stimulus to the person, resulting in a reduction of the person's perception of pain, and/or an improvement in the person's tolerance for pain.

The sensory stimulus provided to the person as described herein may be provided over a period of time and may, in certain embodiments, comprise two or more simultaneous stimuli, such as a visual stimuli and an auditory stimuli. In addition, each sensory stimuli may include a temporal sequence of sensory stimuli patterns, such as a sequence of stimuli having different frequencies, and/or a stimuli that alternates between sensory organs, as by alternating between the eyes or ears or the person. In various embodiments, the stimulus may include, but is not limited to, one or more of: a visual stimuli to one or both eyes of the person; an auditory stimuli to one or both ears of the person; and/or a tactile stimuli to the skin of the person.

Figure 1:
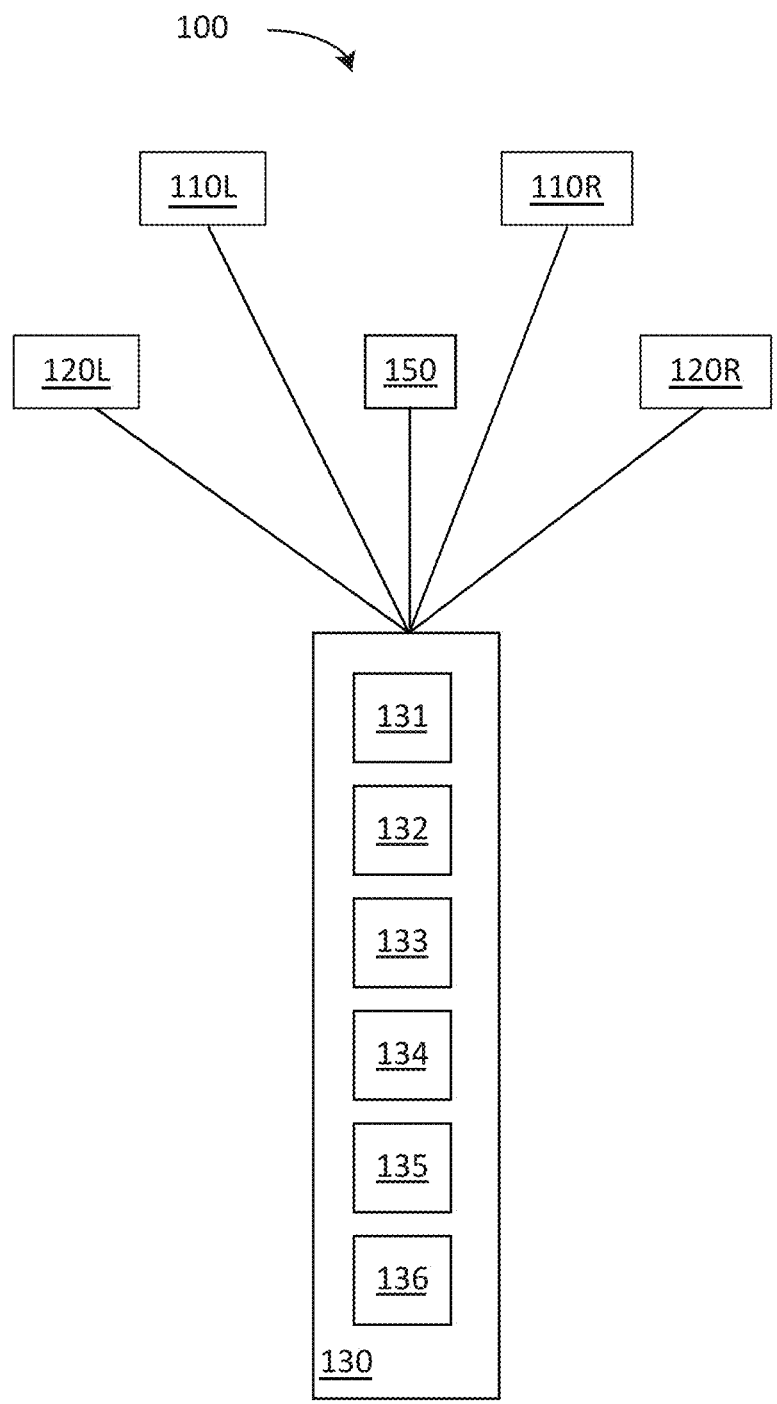
FIG. 1 generally illustrates a schematic diagram of a system that may be used to provide a therapeutic sensory stimulus to a person according to principles of the present disclosure.

FIG. 1 is a schematic diagram of a system 100 that may be used to provide a therapeutic sensory stimulus to a person. The system 100 provides one or more stimuli outputs that a person wearing the system may experience as an auditory stimuli, a visual stimuli, and/or tactile stimuli. In some embodiments, the system 100 comprises a left light source 110L, a right light source 110R, a left vibration source 120L, a right vibration source 120R, and a controller 130 for independently controlling and coordinating the action of the light and vibration sources. Thus, for example, the system 100 may be positioned on the head of a person with the left light source 110L positioned over the left eye to provide a left visual stimulus, the right light source 110R positioned over the right eye to provide a right visual stimulus, the left vibration source 120L positioned to provide left ear auditory stimuli, and the right vibration source 120R positioned to provide right ear auditory stimuli.

In some embodiments, the left and right light sources 110L, 110R may each comprise light-emitting diodes, an incandescent light source having a wavelength filter, a fluorescent light source, a backlit LCD panel, or other light source configured to provide to the person light at a desired, predetermined wavelength or wavelength range.

In some embodiments, the left and right vibration sources 120L, 120R may each comprise earbuds, miniature speakers, or other vibration sources that can provide auditory stimuli to a person. In certain other embodiments, the left and right vibration sources 120L, 120R may comprise bone conduction transducers in the audible frequency range to provide vibrations to the person's skull bone that is sensed as auditory by the person's ear. Optionally, one or more of the left and right vibration sources 120L, 120R may also produce vibrations that are sensed as tactile stimuli. Thus, for example, the controller 130 may provide first signals to bone conduction transducers that vibrate or oscillate at a first frequency that can be interpreted by the person as auditory stimuli and may provide second signals at a second, lower frequency that can be interpreted as a tactile sensation by the person. In other words, bone conduction transducers may be adapted to provide both auditory and tactile stimulus to the person.

In some embodiments, the left and right vibration sources 120L, 120R provide output at specific one or more frequencies or a range of frequencies. In some embodiments, the left and right vibration sources 120L, 120R are separately controlled to provide output at certain times and to not provide output at other times. Thus, for example, a vibration source may be programmed to provide an output as an amplitude modulated audio frequency, which may be, for example and without limitation, 141 Hz, 174 Hz, 232 Hz, or 256 Hz. Thus, in this example, the vibration source is the product of an audio frequency and a square wave.

In some embodiments, the left and right vibration sources 120L, 120R provide signals of slightly different frequencies to the left and right ear. This results in a binaural beats effect, wherein the person perceives a sound at a frequency that is the difference between the frequency in the right ear and the frequency in the left ear. Thus, for example, when a person is provided with a 200 Hz audio frequency to the left ear and a 210 Hz audio frequency to the right ear, the person will perceive 200 Hz in the left ear, 210 Hz in the right ear, and 210 Hz−200 Hz=10 Hz which appear as being provided to both ears. One skilled in the art may use this effect to provide sound at brain wave frequencies separately from, or in combination with, the other methods described herein.

The system 100 may also include a sensor assembly 150 that obtains one or more measurements from the person. Thus, for example and without limitation, the sensor assembly 150 may include, or is in communication with, a sensor that measures some property or characteristic of the person, including but not limited to, heart rate, heart rate variability, body temperature, or blood pressure, and may include electronics that provide a signal indicative of the measurement to the controller 130. In other embodiments, the sensors are connected to the sensor assembly 150 by wired or wireless connectors. Thus, in various embodiments, the sensors may include one or more: electrodes for sensing electrical activity in the brain, as in a 2 or 4 lead EEG, a temperature sensor, and/or a heartbeat sensor, or one or more EMG sensors positioned, for example and without limitation, to measure eye movement to ascertain when REM sleep is reached, and/or to measure muscle tone to aid in determining states of relaxation. In certain embodiments, the controller 130 utilizes the signal from the sensor assembly 150 to modify the intensity and/or timing of the light and vibration sources.

In some embodiments, the controller 130 may include: an output 131 to provide signals to actuate the light sources 110L and 110R, the vibration sources 120L and 120R, and any other components that provide sensory input to the person; an input 132 to accept signals from the sensor assembly 150; a non-transitory memory 133 for storing programming and data for the system 100; a processor 134; and a communications module 135. The memory 133 may include instructions that are accessible to the processor 134 for operating the components that provide sensory input to the person, including but not limited to the light sources 110L and 110R, the vibration sources 120L and 120R, including but not limited to accepting input provided to the input 132 and modifying signals provided to the components that provide sensory input to the person, including but not limited to the light sources 110L and 110R, the vibration sources 120L and 120R. The communications module 135 provides for the transfer of information to or from the controller 130 by wired or wireless means.

In some embodiments, the system 100 may also provide tactile stimulus to a person by including a left tactile stimulus source and a right tactile stimulus source (not shown), each of which may be individually controlled and coordinated with the controller 130 to provide tactile stimuli to a person being treated by the therapeutic system 100.

Figure 2A:
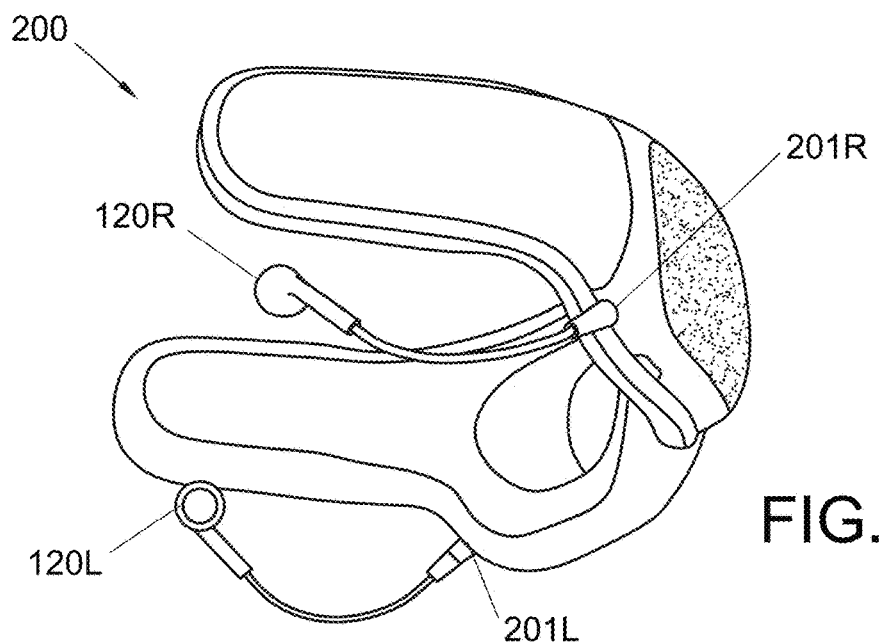
FIGS. 2A, 2B, and 2C generally illustrate a bottom right perspective view, a rear view, and a left view, respectively, of some embodiments of a headset of the system of FIG. 1 according to principles of the present disclosure.
Figure 2B:
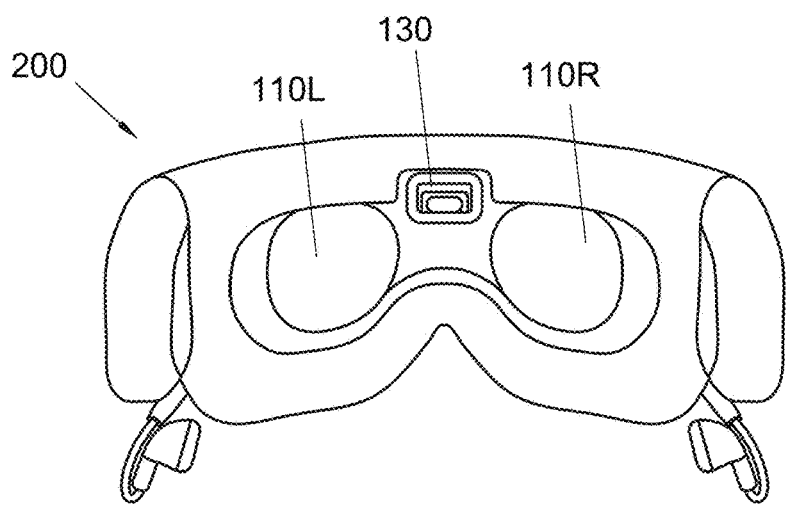
Figure 2C:
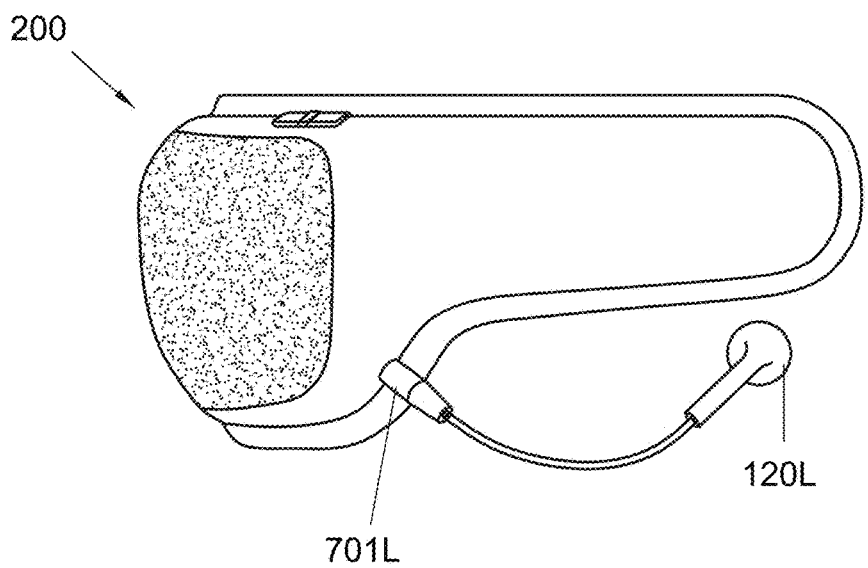
Figure 3:
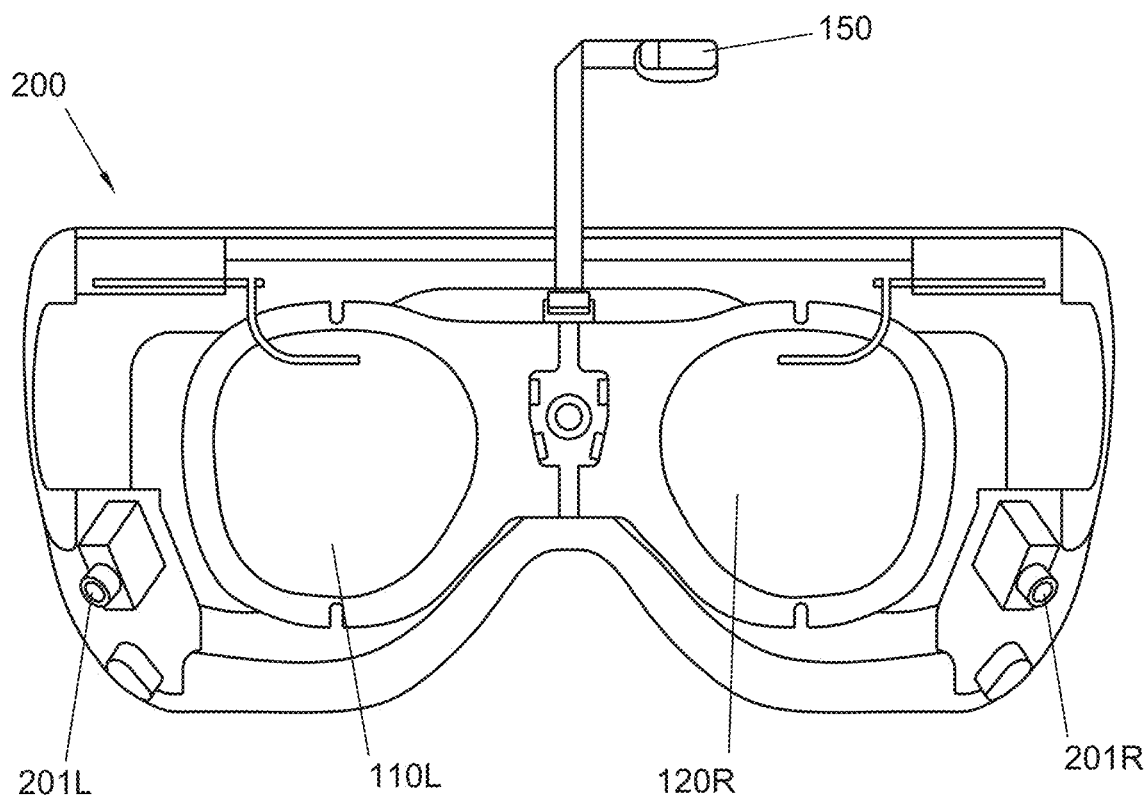
FIG. 3 generally illustrates an exploded front view of some embodiments of the headset of the system of FIG. 1 according to principles of the present disclosure.

FIGS. 2A, 2B, and 2C are a bottom right perspective view, a rear view, and a left view, respectively, and FIG. 3 is an exploded front view of the headset 200, which is generally similar to the system 100 except as explicitly noted.

The headset 100 may include sensor assembly 150, the controller 130, the light sources 110L and 110R, and the vibration sources 120L and 120R. The sensor assembly 150 may also include a biometric sensor system, such as that which is sold under the name of VALENCELL BENCHMARK™ (Raleigh, NC), and may include an infrared light source and detector, which can be used to detect heart rate using pulse oximetry, an accelerator, and a processing unit. The sensor assembly 150 may include a sensor module circuit board that contains a digital optical detector system. This detector may control the LEDs and converts the optical signals reflected from the person's skin to digital format and may communicate over the internal I2C bus to the PerformTek® processor. The accelerometer may read via the internal I2C bus for activity signal.

In some embodiments, the controller 130 may include a Nordic Semiconductor ASA (Oslo, Norway) model NRF51822 Multiprotocol BLUETOOTH® low energy/2.4 GHz RF System on Chip, and a VLSI Solution (Tampere, Finland) model VS1000 audio module.

In some embodiments, the light sources 110L and 110R are Lite-On, Inc. (Milpitas, CA) Bin G3/W2/AU model LTST-020VSKT LEDS. In some embodiments, the vibration sources 120L and 120R are Basen Technology Co, Ltd model PN: OEM-E170a earbuds.

In some embodiments, the sensor assembly 150 may also include a PerformTek® processor which polls sensor data over the internal I2C bus and converts the raw measurements into data registers of biometric values (i.e. Heart Rate, Cadence, VO2) and processes those values further into higher level person assessments (i.e. Calories Burned, Distance, VO2 max, fitness level, and the period between heart rate beats (the Heart Rate Interval, or RR Interval)). The PerformTek® processor may be configured to run algorithms to convert the raw signals to a register array of biometric values and high-level assessments. These values may be available for reading via the UART or I2C firmware interface. In addition, sensor module diagnostics such as signal quality, error codes, and serial number ID may be available.

The sensor assembly 150 may further include control lines for interfacing the controller 130 with the PerformTek® processor, and may further include a Power On Self-Test (POST), UART, or I2C communication interface, and a wake-from-standby line (WAKE). The host processor may be configured to control much of the functionality of the sensor module via a software protocol interface over the UART or I2C interface.

In some embodiments, the sensor assembly 150 may be configured to determine a current heart rate, and/or an inter-beat R-R interval, which may then be provided to the controller 130. In some embodiments, the sensor assembly 150 may also provide accelerometer data to the controller 130.

In yet some embodiments, the sensor assembly 150 may include one or more EEG sensors, as are known in the field, and may provide brain electrical activity measurements to the controller 130.

In some embodiments, the sensor assembly 150 may include one or more EMG sensors positioned, for example and without limitation, to measure eye movement to ascertain when REM sleep is reached, and/or to measure muscle tone to aid in determining states of relaxation. EMG sensors, as are known in the field, may provide brain electrical activity measurements to the controller 130.

The headset 200 may also include the left and right audio jacks 201L and 201R into which the left and right earbuds 120L and 120R, respectively, may be plugged into. Alternatively, stereo headphones (not shown) may be plugged into one of the jacks 201L or 201R, where the jacks are appropriately programmed to provide stereo sound to the headphones.

The headset 200 may be configured to administer a therapeutically effective amount of a sensory stimulus to the person. The sensory stimulus may include one or more visual stimuli and one or more auditory stimuli. The visual stimuli may include at least one of an amplitude modulated light source and a sinusoidally varying light source. The auditory stimuli may include an amplitude modulated audio frequency. The sensory stimulus may include two or more sensory stimuli patterns. At least one of the two or more sensory stimuli patterns may include a first stimuli pattern including a first pulse frequency and a second stimuli pattern including a second pulse frequency. One or more of the first pulse frequency and the second pulse frequency may be between approximately 0.25 Hz and 0.75 Hz, 1.25 Hz and 1.75 Hz, 2 Hz and 4 Hz, 3.75 Hz and 4.25 Hz, or 6 Hz and 9 Hz.

Figure 4:
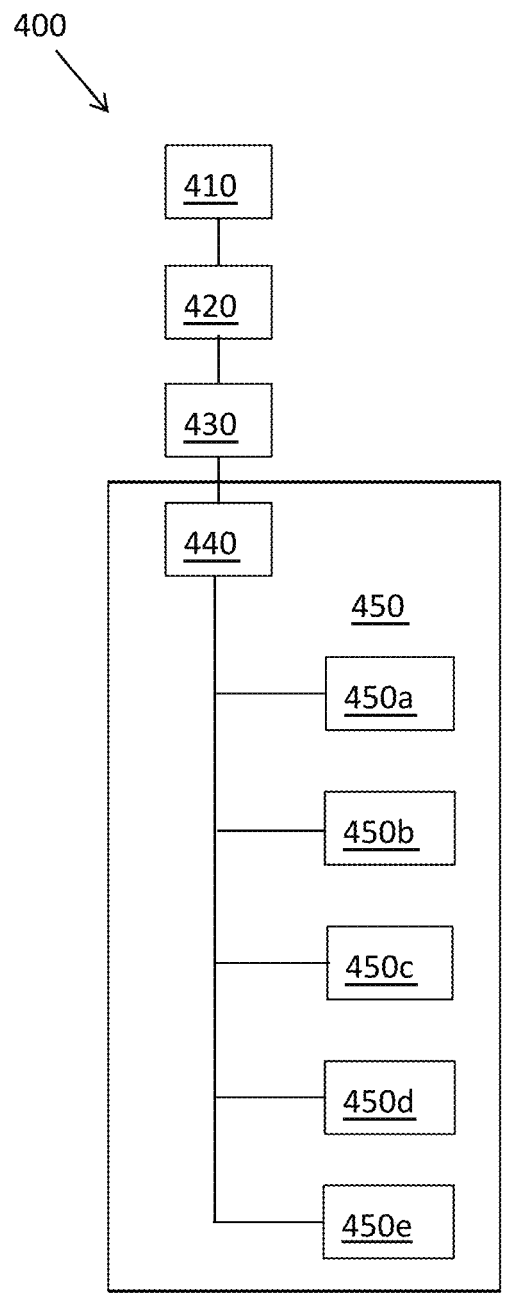
FIG. 4 generally illustrates a flow chart of an exemplary method for providing therapeutic auditory, visual, and/or tactile stimulus according to principles of the present disclosure.

FIG. 4 shows a flow chart of an exemplary method 400 for providing therapeutic auditory, visual, and/or tactile stimulus. The method 400 may use, one of the system 100 or the headset 200 being configured to perform some or all of the steps of the method 400. In a step 410, a subject having pain, or who wishes to undergo a treatment for managing pain, may be identified. In a step 420, the subject may be provided the therapeutic system or headwear, such as the headset 200 as described above, and in step 430, the subject places the headset on their head. In a step 440, the headset 200 may execute the programming 450 provided in the controller 130 to provide stimuli to the subject. The programming may provide two or more of auditory, visual, and/or tactile stimulus to the subject, and thus, for example, may provide power to activate the left light source 110L, the right light source 110R, the left vibration source 120L and or the right vibration source 120R. The programming may also include modifying the auditory, visual, and/or stimuli in response to measurements obtained by the sensor assembly 150 and provided to the controller 130.

As discussed above and herein, the left vibration source 120L and the right vibration source 120R may each comprise bone conduction transducer that may provide both auditory and tactile stimulus.

In certain embodiments, providing two or more of auditory, visual, and/or tactile stimulus concurrently may provide improved therapeutic benefits as compared to providing only one of auditory, visual, or tactile stimulus at one time. The two or more auditory, visual, and/or tactile stimulus may thus combine to provide the improved therapeutic benefits, for example (i.e., the two or more auditory, visual, and/or tactile stimulus may synergize in a way to provide improved results over providing two of the stimuli individually).

Exemplary instructions for providing stimuli may be provided, for example, by the programming 450, which may include one or more subroutines. An exemplary subroutine is subroutine 450e, which can be configured to analyze measurements obtained from sensor assembly 150 and store the analyzed measurements in the memory 113. Another exemplary subroutine 450a may include instructions for the simultaneous activation of all active auditory, visual, and/or tactile stimulus sources. Optionally, the activation of all sources may include the activation of tactile stimulation to run throughout all subsequent auditory and/or visual stimulation. Another exemplary subroutine 450b may include instructions for alternating the left auditory, visual, and/or tactile stimulus sources with the right auditory, visual, and/or tactile stimulus sources (i.e., the left stimuli and right stimuli take turns being active). Another exemplary subroutine 450c may include instructions for alternating the visual sources with the auditory and/or tactile sources (i.e., the visual stimuli and the auditory/tactile stimuli take turns being active). Another exemplary subroutine 450d may include instructions for alternating the left auditory and/or tactile source and the right visual source with the right auditory and/or tactile source and the left visual source (i.e., opposite auditory/tactile stimuli take turns being active).

In certain optional embodiments, one or more of the subroutines 450a, 450b, 450c, or 450d, may be configured to access the analyzed measurements from the subroutine 450e and modify the instructions they provide to the auditory, visual, and/or tactile stimuli depending on real-time or near real-time measurements of the person obtained from the sensor assembly 150. Such programming is further described below.

In step 440, the programming 450, including but not limited to the subroutines 450a, 450b, 450c, and 450d, may be configured to be applied one or more times, individually or in combination with one another. The programming may be configured to further provide sequences of output in the subroutines 450a, 450b, 450c, and 450d at different frequencies and/or timings. Thus, for example, the subroutines may provide output at specific frequencies that change as the subroutine is repeated. The subroutines may be repeated for a predetermined time period. Non-limiting examples of predetermined time periods include approximately 0 to 5 seconds, 5 to 10 seconds, 10 to 15 seconds, 15 to 20 seconds, 20 to 25 seconds, 25 to 30 seconds, 30 to 35 seconds, 35 to 40 seconds, 40 to 45 seconds, 45 to 50 seconds, 50 to 55 seconds, 55 to 60 seconds, 60 to 65 seconds, 65 to 70 seconds, 70 to 75 seconds, 75 to 80 seconds, 80 to 85 seconds, 85 to 90 seconds, 90 to 95 seconds, 95 to 100 seconds, 100 to 105 seconds, 105 to 110 seconds, 110 to 115 seconds, 115 to 120 seconds, 120 to 125 seconds, 125 to 130 seconds, 130 to 135 seconds, 135 to 140 seconds, 140 to 145 seconds, 145 to 150 seconds, 150 to 155 seconds, 155 to 160 seconds, 160 to 165 seconds, 165 to 170 seconds, 170 to 175 seconds, 175 to 180 seconds, 0 to 10 seconds, 5 to 15 seconds, 10 to 20 seconds, 15 to 25 seconds, 20 to 30 seconds, 25 to 35 seconds, 30 to 40 seconds, 35 to 45 seconds, 40 to 50 seconds, 45 to 55 seconds, 50 to 60 seconds, 55 to 65 seconds, 60 to 70 seconds, 65 to 75 seconds, 70 to 80 seconds, 75 to 85 seconds, 80 to 90 seconds, 85 to 95 seconds, 90 to 100 seconds, 95 to 105 seconds, 100 to 110 seconds, 105 to 115 seconds, 110 to 120 seconds, 115 to 125 seconds, 120 to 130 seconds, 125 to 135 seconds, 130 to 140 seconds, 135 to 145 seconds, 140 to 150 seconds, 145 to 155 seconds, 150 to 160 seconds, 155 to 165 seconds, 160 to 170 seconds, 165 to 175 seconds, 170 to 180 seconds, 0 to 15 seconds, 5 to 20 seconds, 10 to 25 seconds, 15 to 30 seconds, 20 to 35 seconds, 25 to 40 seconds, 30 to 45 seconds, 35 to 50 seconds, 40 to 55 seconds, 45 to 60 seconds, 50 to 65 seconds, 55 to 70 seconds, 60 to 75 seconds, 65 to 80 seconds, 70 to 85 seconds, 75 to 90 seconds, 80 to 95 seconds, 85 to 100 seconds, 90 to 105 seconds, 95 to 110 seconds, 100 to 115 seconds, 105 to 120 seconds, 110 to 125 seconds, 115 to 130 seconds, 120 to 135 seconds, 125 to 140 seconds, 130 to 145 seconds, 135 to 150 seconds, 140 to 155 seconds, 145 to 160 seconds, 150 to 165 seconds, 155 to 170 seconds, 160 to 175 seconds, 165 to 180 seconds, 0 to 20 seconds, 5 to 25 seconds, 10 to 30 seconds, 15 to 35 seconds, 20 to 40 seconds, 25 to 45 seconds, 30 to 50 seconds, 35 to 55 seconds, 40 to 60 seconds, 45 to 65 seconds, 50 to 70 seconds, 55 to 75 seconds, 60 to 80 seconds, 65 to 85 seconds, 70 to 90 seconds, 75 to 95 seconds, 80 to 100 seconds, 85 to 105 seconds, 90 to 110 seconds, 95 to 115 seconds, 100 to 120 seconds, 105 to 125 seconds, 110 to 130 seconds, 115 to 135 seconds, 120 to 140 seconds, 125 to 145 seconds, 130 to 150 seconds, 135 to 155 seconds, 140 to 160 seconds, 145 to 165 seconds, 150 to 170 seconds, 155 to 175 seconds, 160 to 180 seconds, 0 to 25 seconds, 5 to 30 seconds, 10 to 35 seconds, 15 to 40 seconds, 20 to 45 seconds, 25 to 50 seconds, 30 to 55 seconds, 35 to 60 seconds, 40 to 65 seconds, 45 to 70 seconds, 50 to 75 seconds, 55 to 80 seconds, 60 to 85 seconds, 65 to 90 seconds, 70 to 95 seconds, 75 to 100 seconds, 80 to 105 seconds, 85 to 110 seconds, 90 to 115 seconds, 95 to 120 seconds, 100 to 125 seconds, 105 to 130 seconds, 110 to 135 seconds, 115 to 140 seconds, 120 to 145 seconds, 125 to 150 seconds, 130 to 155 seconds, 135 to 160 seconds, 140 to 165 seconds, 145 to 170 seconds, 150 to 175 seconds, 155 to 180 seconds, 0 to 30 seconds, 5 to 35 seconds, 10 to 40 seconds, 15 to 45 seconds, 20 to 50 seconds, 25 to 55 seconds, 30 to 60 seconds, 35 to 65 seconds, 40 to 70 seconds, 45 to 75 seconds, 50 to 80 seconds, 55 to 85 seconds, 60 to 90 seconds, 65 to 95 seconds, 70 to 100 seconds, 75 to 105 seconds, 80 to 110 seconds, 85 to 115 seconds, 90 to 120 seconds, 95 to 125 seconds, 100 to 130 seconds, 105 to 135 seconds, 110 to 140 seconds, 115 to 145 seconds, 120 to 150 seconds, 125 to 155 seconds, 130 to 160 seconds, 135 to 165 seconds, 140 to 170 seconds, 145 to 175 seconds, and 150 to 180 seconds.

In certain embodiments, the pulses that determine the amplitude modulation above may be essentially square waves and thus, as determined by a Fourier analysis, may be formed of sinusoidal components at the pulse frequency and at higher harmonics. As an approximation, an ideal square wave with a pulse frequency of P contains only odd-integer harmonic frequencies at $(2k-1)*P$, where $k=1, 2, 3 \ldots$, which contain a fraction $(2/\pi)/(2k-1)$ of the total power in the square wave. Thus, for example, the signal power in a square wave with a pulse frequency of 4 Hz may include 63% of the power at 4 Hz, 21% of the power at 12 Hz, 13% of the power at 20, etc. If the square wave does not have equal on and off periods, then the pulse frequency will also contain even-integer harmonic frequencies.

Thus, for example, subroutine 450a may be configured to provide amplitude modulated auditory output to the vibration source 120R or 120L at a carrier audio frequency of 256 Hz that is turned on and off, that is it is pulsed, at a pulse frequency of 1 Hz for 2 minutes, or may provide amplitude modulated light output to the light source 110R or 110L that produces at a carrier light wavelength 580 nm that is turned on and off, that is it is pulsed at a at a pulse frequency of 1 Hz for 2 minutes. This square pulse auditory or light signal may thus generates signals at a frequency of 1 Hz in addition to higher harmonics. Non-limiting ranges for pulse frequencies may include from approximately 0.5 Hz to 1 Hz, 1 Hz to 2 Hz, 2 Hz to 3 Hz, 3 Hz to 4 Hz, 4 Hz to 5 Hz, 5 Hz to 6 Hz, 6 Hz to 7 Hz, 7 Hz to 8 Hz, 8 Hz to 9 Hz, 9 Hz to 10 Hz, 10 Hz to 11 Hz, 11 Hz to 12 Hz, 12 Hz to 13 Hz, 13 Hz to 14 Hz, 14 Hz to 15 Hz, 15 Hz to 16 Hz, 16 Hz to 17 Hz, 17 Hz to 18 Hz, 18 Hz to 19 Hz, 19 Hz to 20 Hz, 1 Hz to 3 Hz, 2 Hz to 4 Hz, 3 Hz to 5 Hz, 4 Hz to 6 Hz, 5 Hz to 7 Hz, 6 Hz to 8 Hz, 7 Hz to 9 Hz, 8 Hz to 10 Hz, 9 Hz to 11 Hz, 10 Hz to 12 Hz, 11 Hz to 13 Hz, 12 Hz to 14 Hz, 13 Hz to 15 Hz, 14 Hz to 16 Hz, 15 Hz to 17 Hz, 16 Hz to 18 Hz, 17 Hz to 19 Hz, 18 Hz to 20 Hz, 1 Hz to 4 Hz, 2 Hz to 5 Hz, 3 Hz to 6 Hz, 4 Hz to 7 Hz, 5 Hz to 8 Hz, 6 Hz to 9 Hz, 7 Hz to 10 Hz, 8 Hz to 11 Hz, 9 Hz to 12 Hz, 10 Hz to 13 Hz, 11 Hz to 14 Hz, 12 Hz to 15 Hz, 13 Hz to 16 Hz, 14 Hz to 17 Hz, 15 Hz to 18 Hz, 16 Hz to 19 Hz, 17 Hz to 20 Hz. Non-limiting examples of ranges for carrier light wavelength may include from approximately 380 nm to 400 nm, 390 nm to 410 nm, 400 nm to 420 nm, 410 nm to 430 nm, 420 nm to 440 nm, 430 nm to 450 nm, 440 nm to 460 nm, 450 nm to 470 nm, 460 nm to 480 nm, 470 nm to 490 nm, 480 nm to 500 nm, 490 nm to 510 nm, 500 nm to 520 nm, 510 nm to 530 nm, 520 nm to 540 nm, 530 nm to 550 nm, 540 nm to 560 nm, 550 nm to 570 nm, 560 nm to 580 nm, 570 nm to 590 nm, 580 nm to 600 nm, 590 nm to 610 nm, 600 nm to 620 nm, 610 nm to 630 nm, 620 nm to 640 nm, 630 nm to 650 nm, 640 nm to 660 nm, 650 nm to 670 nm, 660 nm to 680 nm, 670 nm to 690 nm, and 680 nm to 700 nm. One or more of the non-limiting examples of pulse frequencies may be used in conjunction with one or more of the non-limiting examples of carrier wavelength.

In certain embodiments, the subroutines described herein generate pulses having sinusoidal components that correspond with certain known brain wave frequencies (i.e., frequencies of neural oscillations, or repetitive patterns of activity in the brain), which are generally accepted as being delta waves (0.1 to 4.0 Hz), theta brain waves (4 to 7 Hz), alpha brain waves (8 to 15 Hz), beta brain waves (16 to 31 Hz), and gamma brain waves (32 to 100 Hz). A person skilled in the art will appreciate that the precise boundaries of these ranges may vary from those provided in the present disclosure, and other ranges for delta brain waves, theta brain waves, alpha brain waves, beta brain waves, and gamma brain waves can be considered without departing from the present disclosure. Thus, certain embodiments may include pulse frequencies from approximately 3.75 Hz to 4.25 Hz (theta brain waves), from 1.25 Hz to 1.75 Hz (delta brain waves), and/or from 0.25 Hz and 0.75 Hz (delta brain waves). Other non-limiting ranges for pulse frequencies may include from approximately 0.5 Hz to 1 Hz (delta brain waves), 1 Hz to 2 Hz (delta brain waves), 2 Hz to 3 Hz (delta brain waves), 3 Hz to 4 Hz (delta brain waves), 4 Hz to 5 Hz (theta brain waves), 5 Hz to 6 Hz (theta brain waves), 6 Hz to 7 Hz (theta brain waves), 7 Hz to 8 Hz (beta brain waves), 8 Hz to 9 Hz (beta brain waves), 9 Hz to 10 Hz (beta brain waves), 10 Hz to 11 Hz (beta brain waves), 11 Hz to 12 Hz (beta brain waves), 12 Hz to 13 Hz (beta brain waves), 13 Hz to 14 Hz (beta brain waves), 14 Hz to 15 Hz (beta brain waves), 15 Hz to 16 Hz (beta brain waves), 16 Hz to 17 Hz (beta brain waves), 17 Hz to 18 Hz (beta brain waves), 18 Hz to 19 Hz (beta brain waves), 19 Hz to 20 Hz (beta brain waves), 1 Hz to 3 Hz (delta brain waves), 2 Hz to 4 Hz (delta brain waves), 3 Hz to 5 Hz (delta/theta brain waves), 4 Hz to 6 Hz (theta brain waves), 5 Hz to 7 Hz (theta brain waves), 6 Hz to 8 Hz (theta/beta brain waves), 7 Hz to 9 Hz (beta brain waves), 8 Hz to 10 Hz (beta brain waves), 9 Hz to 11 Hz (beta brain waves), 10 Hz to 12 Hz (beta brain waves), 11 Hz to 13 Hz (beta brain waves), 12 Hz to 14 Hz (beta brain waves), 13 Hz to 15 Hz (beta brain waves), 14 Hz to 16 Hz (beta brain waves), 15 Hz to 17 Hz (beta brain waves), 16 Hz to 18 Hz (beta brain waves), 17 Hz to 19 Hz (beta brain waves), 18 Hz to 20 Hz (beta brain waves), 1 Hz to 4 Hz (delta brain waves), 2 Hz to 5 Hz (delta/theta brain waves), 3 Hz to 6 Hz (delta brain waves), 4 Hz to 7 Hz (theta brain waves), 5 Hz to 8 Hz (theta/beta brain waves), 6 Hz to 9 Hz (theta/beta brain waves), 7 Hz to 10 Hz (beta brain waves), 8 Hz to 11 Hz (beta brain waves), 9 Hz to 12 Hz (beta brain waves), 10 Hz to 13 Hz (beta brain waves), 11 Hz to 14 Hz (beta brain waves), 12 Hz to 15 Hz (beta brain waves), 13 Hz to 16 Hz (beta brain waves), 14 Hz to 17 Hz (beta brain waves), 15 Hz to 18 Hz (beta brain waves), 16 Hz to 19 Hz (beta brain waves), 17 Hz to 20 Hz (beta brain waves). Further, individual pulse frequencies may vary within these ranges (e.g., shifting from 18.5 Hz to 16.5 Hz, while remaining in the 16 Hz to 19 Hz range).

Further, multiple pulse frequencies may be provided sequentially or at the same time. For example, a first pulse frequency may include a range of frequencies of approximately 12 Hz to 14 Hz, a second pulse frequency following the first pulse frequency may include a range of frequencies of approximately 8 Hz to 10 Hz range, a third pulse frequency following the second pulse frequency may include a range of frequencies of approximately 5 Hz to 6 Hz range, and a fourth pulse frequency following the third pulse frequency may include a range of frequencies of approximately 3.75 Hz range to a 4.25 Hz range. In some embodiments, different pulse frequencies or segments associated with different pulse frequencies may be distinguishable from one another by discontinuities in frequency (e.g., a first pulse frequency in a range of frequencies of approximately 6.6 Hz to 8 Hz being immediately followed by another pulse frequency in range of frequencies of approximately 4 Hz to 6.3 Hz), while in other embodiments, different pulse frequencies or segments associated with different pulse frequencies may be distinguishable from one another by changes in a rate of change of the pulse frequency (e.g., a decreasing pulse frequency in range of frequencies of approximately 4 Hz to 6 Hz being immediately followed by an increasing pulse frequency in range of frequencies of approximately 4 Hz to 5.2 Hz or a first increasing pulse frequency in range of frequencies of approximately 3.9 Hz to 4.4 Hz being immediately followed by a second increasing pulse frequency in range of frequencies of approximately 4.4 Hz to 6 Hz that is increasing in frequency more rapidly than the first increasing pulse frequency was increasing). Further, differences between stimuli patterns can include differences other than pulse frequency. As non-limiting examples, stimuli patterns may be different in duration, intensity (i.e., peak amplitude), or wavelength (i.e., color or pitch).

In addition, by altering the output between left and right channels, the brain may be stimulated in a way that it is forced to communicate between the left and right sides of the brain. This forced communication, for example, can allow PTSD memories to be wired to both sides of the brain, thereby stopping undesirable flashbacks. It can also create an enhanced relaxation effect, allowing for deeper relaxation and pain management.

In some embodiments, the system 100 may be configured to provide a stimulus that may include visual and auditory stimuli over three temporally sequential segments—a first segment where stimuli occurs at a first frequency, followed by a second segment where stimuli occurs at a second frequency, which was followed by a third segment where stimuli occurs at a third frequency. Each time segment included sub-segments of visual and auditory stimuli, where each sub-segment was determined by one of the subroutines described above, for example. The visual stimuli were provided by pulsing light at a wavelength of 580 nm at certain pulse frequencies and by pulsing auditory signals at a frequency of 256 Hz at certain pulse frequencies, though a person having skill in the art will understand that other wavelengths and other pulse frequencies may also be considered.

In some embodiments, a treatment stimulus lasted for 16 minutes, and may be understood by reference to Table 500 in FIG. 5, Table 600 in FIG. 6, and Table 700 in FIG. 7, where Table 500 contains specifications for the first segment ("Segment A"), Table 600 contains specifications for the next, second time segment ("Segment B"), and Table 700 contains specifications for the last time segment ("Segment C"). Each of the Segments stimuli patterns at a different pulse frequency. Specifically, Segment A cycles the stimuli through a block of four Segment A stimuli patterns for a total of 2 minutes, Segment B cycles the stimuli through a block of four Segment B stimuli patterns for a total of 2 minutes, and Segment C cycles the stimuli through a block of six Segment C stimuli patterns for a total of 12 minutes.

More specifically, in the four Segment A stimuli patterns, as shown in Table 500 as Blocks A1, A2, A3, and A4 respectively, the auditory and light outputs cycle 115 or 116 times between being on for 0.1277 seconds and then being off for 0.1277 seconds (that is, at a pulse frequency of 3.9 Hz), followed by no output for 0.5 seconds. In the Segment B stimuli patterns, as shown in Table 600 as Blocks B1, B2, B3 and B4, the auditory and light outputs cycle 44 or 45 times between being on for 0.3333 seconds and then being off for 0.3333 seconds (that is, at a pulse frequency of 1.5 Hz) followed by no output for 0.5 seconds. In the Segment C stimuli patterns, as shown in Table 700 and labeled Blocks C1, C2, C3 and C4, the auditory and light outputs cycle 14 or 15 times between being on for 1 second and then being off for 1 second (that is, a pulse frequency of 0.5 Hz), followed by no output for 1 second. Blocks A1, B1, and C1 pulse the right and left sides of both the light and auditory together, with all outputs are synchronized to be on or off at the same time, as provided by the subroutine 450a. Blocks A2, B2, and C2 synchronize the left side light and auditory output, and the right side light and auditory output to be opposite to one another, as provided by the subroutine 450b. Blocks A3, B3, and C3 synchronize both lights together to be opposite to both auditory outputs, as provided by subroutine the 450c. Blocks A4, B4, and C4 synchronize the right auditory and light to be opposite to the left auditory and light outputs, as provided by subroutine 450d.

Other examples segmented stimuli patterns include treatment lasting for a total of approximately 16 minutes. This example starts with a first pulse frequency of approximately 20 Hz, followed by a second pulse frequency that decreases over time to approximately 1 Hz, followed by a third pulse frequency that increases over time to approximately 17 Hz, followed by further pulse frequencies that continue to increase and decrease while narrowing in on an extended period at a steady pulse frequency of approximately 5 Hz for approximately 4 to 5 minutes, and returning to a final pulse frequency of 20 Hz.

In step 440, the subroutine 450e may be configured to receive measurements from the sensor assembly 150 and store analyzed measurements. In some embodiments, the sensor assembly 150 may be configured to provide instantaneous, or nearly instantaneous, measurements from the person. Thus, for example and without limitation, the sensor assembly 150 may provide a sequence of measurements of beat-to-beat intervals of the heart of the person, that is, the time interval between the last two heart beats, which is also referred to, without limitation, as the RR intervals. The controller 130 may be configured to compute and store values of the heart rate variability (HRV), which is a mathematical representation of the physiological phenomenon of variation in the time interval between heartbeats.

In certain embodiments, a time-domain calculation of RR intervals, as obtained by the sensor assembly 150, may be used to compute the HRV. Thus, for example, the sequence of RR intervals ("RRi") may be accepted from the sensor assembly 150 and stored in the memory 133. After the accumulation RRi for a period of time, T, the HRV may be calculated as approximated by the root mean square of successive differences between adjacent RRs, or RMSSD. Thus, at a time T from the beginning of the accumulation of data, if N consecutive RR intervals are stored in the memory 133, the following calculation may be performed in the processor 134 according to a program stored in the memory:

$$RMSSD = \sqrt{\frac{1}{N-1}\left(\sum_{i=1}^{N-1}(RR_{i+1} - RR_i)^2\right)}$$

The initial value of RMSSD (that is, RMSSD0) may be stored in the memory 133 as a baseline. Thereafter, at the end of each period T, the calculation of RMSSD may be repeated covering that time period. As a result, a sequence of RMSSDj values may be computed. Next the difference between the current RMSSD value and the baseline RMSSD0 may be computed as ΔRMSSDj=RMSSDj−RMSSD0. ΔRMSSD is a measure of the change between the current HRV and the baseline, initial HRV.

In general, it is realized by those skilled in the art, that an increased in HRV may be associated with a relaxed state, or a sleep state, and that a decrease in HRV may be associated with a less relaxed, or stressed, state. For uses of the therapeutic system 100 intended to calm a person or to induce sleep, a positive ARMSSD may indicate that the person is becoming relaxed and that the system is working as intended. A negative ARMSSD may indicate that the person is not becoming more relaxed. In some embodiments, an indication that the person is relaxed (ΔRMSSD>0) may be used to modify the treatment by reducing the treatment time and/or intensity of the stimuli, and an indication that the person is less relaxed (ΔRMSSD<0) may be used to modify the treatment to increase the treatment time and/or the intensity of the stimuli.

In certain embodiments, Kubios HRV software (manufactured by Kuopio, Finland) may be used to analyze the RR intervals to provide additional HRV related data. Thus, for example, one useful measure for analyzing HRV may be the fraction of the power of the HRV signal that occurs in certain frequency ranges. Thus, for example, one measure which is referred to herein as HRV-HFnu may be obtained by taking the Fourier transform of the HRV signal and computing the ratio of the power of the HRV signal from 0.15 to 0.40 Hz ("high frequencies") to the total power of the HRV signal.

The calculations described above are provided by way of explanation and are not meant to limit the scope of the calculations or how the operation of the therapeutic system 100 is or is not modified using HRV measurements.

Although the above steps show the method 400 of treating a patient in accordance with certain embodiments, a person of ordinary skill in the art will recognize many variations based on the teaching described herein. The steps may be completed in a different order. Steps may be added or deleted. Some of the steps may comprise sub-steps. Many of the steps may be repeated as often as beneficial to the treatment.

One or more of the steps of the method 400 may be performed with the circuitry as described herein, for example, circuitry of the controller 130 or the external control unit 130a such as one or more of a processor or logic circuitry such as a central processing unit (CPU) or a programmable array logic for field programmable gate array. The circuitry may be programmed to provide one or more of the steps of the method 400, and the program may comprise program instructions stored on a computer readable memory or programmed steps of the logic circuitry such as the programmable array logic or the field programmable gate array, for example.

A Study of the Treatment of Fibromyalgia

A study was conducted on the effectiveness of the method for treating fibromyalgia using the headset 200. A single arm trial was conducted by PI Dr. Mark Kuchar, D C, CSCS at Southpointe Clinic, Colorado.

Protocol

A group of 8 participants were selected for testing the effectiveness of the headset 200 in treating fibromyalgia. Each of the participants were considered to be treatment resistant—that is, they experienced no improvement from other modalities or placebo and had previously failed on all drug regimens and a 90 day best standard of care protocol.

The study was divided into 3 phases: Screening and Baseline, Treatment, and Follow-up. Each patient participated in the study for up to 32 days, including Screening and Baseline (up to 7 days), Treatment (15 days), and Follow-up (up to 10 days).

Screening and Baseline procedures were performed within 7 days of admission to the Treatment Phase. Participants were instructed to rate their pain intensity and sleep quality, and record their concomitant medication use on a daily basis using a logbook.

On Day 1 of the Treatment Phase, eligible participants were instructed on the use of receiving a treatment from the headset 200 and used the device for the first time under clinic supervision; all other uses of the device were conducted at home. During the Treatment Phase, participants underwent at least 2 daily treatments with the headset 200, including a treatment immediately prior to bedtime. Additional treatments were allowed, as needed (PRN), at the participant's discretion.

Pain intensity was assessed, as described subsequently, prior to each treatment and, with the exception of the bedtime treatment, within 5 minutes of completion of each treatment. Participants recorded pain intensity and sleep quality, as discussed subsequently, upon waking in the morning, and recorded the use of medications/non-pharmacological therapies on a daily basis prior to bedtime.

During the Treatment Phase, participants attended the study site on Day 1 of the Treatment Phase, and on Day 15 of the Treatment Phase. At each study visit, assessments of sleep quality, depression and anxiety, use of concomitant medications/non-pharmacological therapies and compliance with the headset 200 were completed. On Day 8 of the Treatment Phase (+/−1 day) participants received a phone call to confirm compliance with use of the headset 200, answer questions and check for adverse events (AEs). Assessments of AEs and treatment acceptability were also be conducted during the Treatment Phase. A Follow-up call was scheduled within 7 days (±3 days) of completing the Treatment Phase.

The following concomitant medications and therapies were permitted during the study:

Nonsteroidal anti-inflammatory drugs (NSAIDs) were permitted occasionally for headache, fever, or other indications aside from chronic pain, for no more than 3 consecutive days and no more than the maximum daily recommended dose. NSAIDs were not be permitted during the Baseline period and the last 3 days of the Treatment Phase.

Opioid and non-opioid analgesics were permitted, but participants were required to be on a stable dose (±20% dose and timing of administration) for at least 14 days prior to enrollment.

Anti-constipation medications.

Aspirin at doses ≤325 mg/day for cardiovascular prophylaxis.

The following medications and therapies were permitted, and remained stable (±20% dose and timing of administration) throughout the duration of the participant's participation in the study: muscle relaxants, hypnotics (eszopiclone, zolpidem, zaleplon), antidepressants, anticonvulsants, benzodiazepines, physical therapy, biofeedback therapy, acupuncture therapy, and herbal remedies (except for St. John's Wort).

On a case-by-case basis, the investigator was permitted to allow the use of some concomitant medications, for example, to treat an AE, as long as the investigator determined that the medication would not affect the patient's safety or study integrity. The following regimens were permitted:

Supplemental medications including either 1000 mg acetaminophen up to 2 times per day, 550 mg naproxen up to 2 times per day, or 800 mg/day ibuprofen up to 4 times per day, up to the maximum daily dose (i.e., either up to 2000 mg/day acetaminophen, up to 1100 mg/day naproxen, or up to 3200 mg/day ibuprofen).

Use of any analgesic medications or non-pharmacological therapies where be recorded (date, time, medication name, dose, regimen, etc.).

All 8 participants elected to continue using the device and stated an intention to use it as part of their treatment regimen, and one participant was able to discontinue use of alprazolam (Xanax) early in study.

Measures of Symptoms of Fibromyalgia

In the study discussed subsequently, test subjects were provided with a number of sensory stimuli and their response to the treatment was determined using subjective measures using the following questionnaires:

Pain Intensity Visual Analog Scale (VAS) (or "VAS-Pain"), which prompts the patient to rate "How I feel" on a VAS, ranging from between "No Pain," which is assigned a value of zero, to "Worst Pain Imaginable,"

which is assigned a value of 100. See, for example, img.medscape.com/article/742/580/VAS.pdf.

Pittsburgh Sleep Quality Index (PSQI), which presents questions used to measure the quality and patterns of sleep in adults). It differentiates "poor" from "good" sleep quality by measuring seven areas (components): subjective sleep quality, sleep latency, sleep duration, habitual sleep efficiency, sleep disturbances, use of sleeping medications, and daytime dysfunction over the last month. See, for example https://www.opapc.com/uploads/documents/PSQI.pdf. The score on the PSQI ranges from 0-21, where higher scores indicate worse sleep quality.

Patient Health Questionnaire (PHQ-9), which presents questions related to depression. The PHQ-9 is a validated tool for screening, diagnosing, monitoring and measuring depression severity, and scores each of the 9 Diagnostic and Statistical Manual of Mental Disorder, Fourth Edition (DSM-IV) related criteria.

Generalized Anxiety Disorder 7-item (GAD-7) Scale, presents question to the patient for screening and measuring severity of generalized anxiety. See, for example https://www.mdcalc.com/gad-7-general-anxiety-disorder-7. The score on the GAD-7 Scale range from 0-21, where a score of 5-9 is interpreted as a level of mild anxiety, a score of 10-14 is interpreted as a moderate level of anxiety, having possible clinical significance, and a score of 15 or greater is interpreted as a severe level of anxiety, likely warranting active treatment.

Patient Global Impression of Change (PGIC) is a commonly used tool that is recommended to assess a patient's overall satisfaction with their treatment. The patent is prompted to indicate whether there has been any change in their activity limitations, symptoms, emotions and overall quality of life, as related to their pain condition, since the start of the study (1=No change to 7=A great deal better). In addition, patients rate the degree of change since beginning treatment on a 0 (Much Better) to 10 (Much Worse) scale. Patients completed the PGIC on Day 15 or early discontinuation.

Likelihood to Use Device Again question, in which patients answered the question "If the device was available, how likely would you be to continue use of the device," of the headset 200. Response options range from extremely likely, very likely, somewhat likely, not very likely, to not at all likely.

Study Results

The following is a comparison of the average baseline measures if pain, anxiety, depression, quality of sleep for all 8 participants with the same measures after the Treatment Phase.

The average VAS-Pain score for all study participants was 62.7 at baseline and 46.5 at the end of treatment, with a P value of 0.0754. This is a 26% decrease in the VAS-Pain score, corresponding to a decrease in perceived pain from "intense" to "distressing." Further, it was found that the treatment worked best for participants with the greatest amount of pain, as those with the severest amounts of pain patients had a reduction of VAS-Pain scores of 49%.

The average GAD 7 scale scores, which is a measure of anxiety, was 11 at baseline and 6.25 at the end of treatment, with a P value of 0.0096, which indicates a high level of level of statistical certainty. This is a 43% decrease in the anxiety scores and corresponds to a decrease in perceived anxiety from "moderate" to "mild."

The average PHQ9 scale scores, which is a measure of depression was 15.5 before the study and 8.75 at the end of treatment, with a P value of 0.0024, which indicates a high level of level of statistical certainty. This is a 44% decrease in the anxiety scores and corresponds to a decrease in perceived depression from "moderately severe" to "mild."

Figure 8:
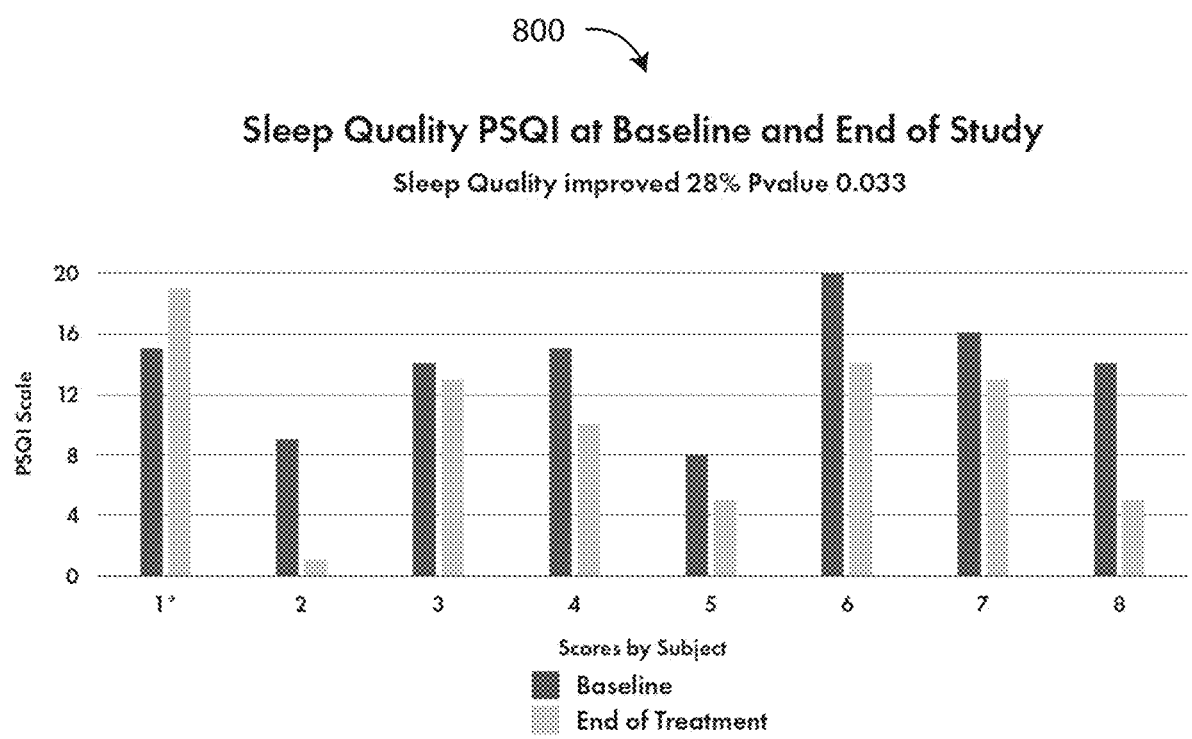
FIG. 8 generally illustrates a graph showing treatment results according to principles of the present disclosure.

The PSQI scale scores for each participant is shown in graph 800 of FIG. 8. The results indicate that the quality of sleep improved by 28% over the course of treatment, with a P value of 0.0033, which indicates a high level of level of statistical certainty.

The results of the Likelihood to Use Device Again survey at the end of the Treatment Phase indicated that 6 of 8 of the participants would be "Very Likely" to use the device, if it was offered to them.

The results of the Quality of Life Likelihood to Adopt Device survey at the end of the Treatment Phase indicated that 6 of 8 of the participants would be "Very Likely" to use the device, if it was offered to them.

The results of the Patient Global Impression of Change (PGIC) survey shows that most patients indicated that the Treatment Phase provided a "Definite improvement that has made a real and worthwhile difference" or higher on the PGIC survey and provided an improvement in the quality of life.

Some embodiments of each of the methods described herein is in the form of a computer program that executes on a processing system, e.g., one or more processors that are part of the system 100. Thus, as will be appreciated by those skilled in the art, embodiments of the present disclosure may be embodied as a method, an apparatus such as a special purpose apparatus, an apparatus such as a data processing system, or a carrier medium, e.g., a computer program product. The carrier medium carries one or more computer readable code segments for controlling a processing system to implement a method. Accordingly, aspects of the present disclosure may take the form of a method, an entirely hardware embodiment, an entirely software embodiment or an embodiment combining software and hardware aspects. Furthermore, the present disclosure may take the form of carrier medium (e.g., a computer program product on a computer-readable storage medium) carrying computer-readable program code segments embodied in the medium. Any suitable computer readable medium may be used, including a magnetic storage device (e.g., a diskette or a hard disk), a solid state memory, or an optical storage device (e.g., a CD-ROM).

Reference throughout this specification to "some embodiments" or "an embodiment" means that a particular feature, structure or characteristic described in connection with the embodiment is included in at least some embodiments of the present disclosure. Thus, appearances of the phrases "in some embodiments" or "in an embodiment" in various places throughout this specification are not necessarily all referring to the same embodiment, nor necessarily all referring to different embodiments. Furthermore, the particular features, structures or characteristics may be combined in any suitable manner, as would be apparent to one of ordinary skill in the art from this disclosure, in one or more embodiments.

Similarly, it should be appreciated that in the above description of exemplary embodiments of the disclosure, various features of the disclosure are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment.

Thus, the claims following the Detailed Description are hereby expressly incorporated into this Detailed Description, with each claim standing on its own as a separate embodiment of this disclosure.

Consistent with the above disclosure, the examples of systems and methods enumerated in the following clauses are specifically contemplated and are intended as a non-limiting set of examples.

Clause 1. A method of treating fibromyalgia, comprising:
administering a therapeutically effective amount of a sensory stimulus to a person, wherein the sensory stimulus includes one or more visual stimuli and one or more auditory stimuli.

Clause 2. The method of the preceding clause, further comprising:
treating one or more symptoms of fibromyalgia, wherein the one or more symptoms are selected from a group including anxiety, pain, depression, and one or more sleep disorders.

Clause 3. The method of any preceding clause, wherein at least one of the one or more visual stimuli includes an amplitude modulated light source.

Clause 4. The method of any preceding clause, wherein at least one of the one or more visual stimuli includes a sinusoidally varying light source.

Clause 5. The method of any preceding clause, wherein at least one of the one or more auditory stimuli includes an amplitude modulated audio frequency.

Clause 6. The method of any preceding clause, wherein the sensory stimulus includes two or more sensory stimuli patterns.

Clause 7. The method of any preceding clause, wherein at least one of the two or more sensory stimuli patterns includes a first stimuli pattern comprising a first pulse frequency and a second stimuli pattern comprising a second pulse frequency.

Clause 8. The method of any preceding clause, wherein at least one of the first pulse frequency and the second pulse frequency is between approximately 0.25 Hz and 0.75 Hz, 1.25 Hz and 1.75 Hz, 2 Hz and 4 Hz, 3.75 Hz and 4.25 Hz, or 6 Hz and 9 Hz.

Clause 9. The method of any preceding clause, wherein the first stimuli pattern includes a pulse frequency between approximately 0.25 Hz and 0.75 Hz, 1.25 Hz and 1.75 Hz, 2 Hz and 4 Hz, 3.75 Hz and 4.25 Hz, or 6 Hz and 9 Hz; and
wherein the second stimuli pattern includes a pulse frequency that is between approximately 0.25 Hz and 0.75 Hz, 1.25 Hz and 1.75 Hz, 2 Hz and 4 Hz, 3.75 Hz and 4.25 Hz, or 6 Hz and 9 Hz.

Clause 10. The method of any preceding clause, wherein the two or more sensory stimuli patterns include a third stimuli pattern, wherein the third stimuli pattern is different from the first stimuli pattern and the second stimuli pattern.

Clause 11. The method of any preceding clause, wherein the sensory stimulus alternates between
a first sensory stimuli including simultaneously providing a left visual stimuli pattern to a left eye of the person and a right auditory stimuli pattern to a right side of a head of the person, and
a second sensory stimuli including simultaneously providing a right visual stimuli pattern to a right eye of the person and a left auditory stimuli pattern to a left side of the head of the person,
wherein one or more of the left auditory stimuli patterns and the right auditory stimuli patterns comprises a sequence of stimuli patterns including a first stimuli pattern, a second stimuli pattern, and a third stimuli pattern.

Clause 12. The method of any preceding clause, further comprising:
periodically providing a sensory stimuli including simultaneously providing a left visual stimuli pattern to the left eye of the person, a right visual stimuli pattern to the right eye of the person, a left auditory stimuli pattern to the left side of the head, and a right auditory stimuli pattern to the right side of the head of the person.

Clause 13. The method of any preceding clause, further comprising:
alternating sensory stimuli between
a third sensory stimuli including simultaneously providing a left visual stimuli pattern to the left eye of the person and a left auditory stimuli pattern to the left side of the head, and
a fourth sensory stimuli including simultaneously providing a right visual stimuli pattern to the right eye of the person and a right auditory stimuli pattern to the right side of the head of the person.

Clause 14. The method of any preceding clause, further comprising:
alternating sensory stimuli between
a fifth sensory stimuli including simultaneously providing a left auditory stimuli pattern to the left side of the head and a right auditory stimuli pattern to the right side of the head, and
a sixth sensory stimuli including simultaneously providing a left visual stimuli pattern to the left eye of the person and a right visual stimuli pattern to the right eye of the person.

Clause 15. The method of any preceding clause, further comprising:
providing a headset to be worn on a head of the person; and
wherein the left auditory stimuli pattern comprises generating the left auditory stimuli pattern with a left bone conduction transducer of the headset; and wherein the right auditory stimuli pattern comprises generating the right auditory stimuli pattern with a right bone conduction transducer of the headset.

Clause 16. The method of any preceding clause, wherein one or more of the left auditory stimulus pattern or the right auditory stimuli pattern includes an auditory frequency of approximately 240 Hz to 480 Hz.

Clause 17. The method of any preceding clause, wherein one or more of the left visual stimuli pattern or right visual stimuli pattern comprises repeatedly pulsing a light at one or more of a first pulse frequency, a second pulse frequency less than the first pulse frequency, or a third pulse frequency less than the first pulse frequency and the second pulse frequency.

Clause 18. The method of any preceding clause, wherein at least one of the first stimuli pattern, the second stimuli pattern, the third stimuli pattern, or repeatedly pulsing a light occurs for a predetermined time interval.

Clause 19. The method of any preceding clause, wherein the predetermined time interval is between approximately 25 and 45 seconds.

Clause 20. The method of any preceding clause, wherein the sequence of stimuli patterns each include a pulse frequency including a pulse period, wherein a portion of the pulse period includes a stimulus of an auditory frequency of between approximately 240 Hz and 480 Hz.

Clause 21. The method of any preceding clause, wherein the portion of the pulse period is one half of the pulse period.

Clause 22. The method of any preceding clause, wherein one or more of the first stimuli pattern, the second stimuli pattern, or the third stimuli pattern includes a pulse frequency corresponding to a delta brain wave frequency, a theta brain wave frequency, or an alpha brain wave frequency.

Clause 23. The method of any preceding clause, further comprising:
  obtaining a measurement of the person using a sensor;
  determining a state of the person from the obtained measurement; and
  modifying the sensory stimulus according to the state of the person.

Clause 24. The method of any preceding clause, wherein the sensor comprises at least one of a heart rate sensor, a heart rate variability (HRV) sensor, a temperature sensor, a motion sensor, a galvanic skin response sensor, an accelerometer, an EEG, and an EMG.

Clause 25. The method of any preceding clause, wherein the state of the person comprises a state of sleep or a level or a change in a level of relaxation or a level of arousal.

Clause 26. A system for treating fibromyalgia, comprising:
  a headset configured to be worn on a head of a person;
    wherein the headset is configured to administer a therapeutically effective amount of a sensory stimulus to the person; and wherein the sensory stimulus includes one or more visual stimuli and one or more auditory stimuli.

Clause 27. The system of any preceding clause, wherein at least one of the one or more visual stimuli includes at least one of an amplitude modulated light source and a sinusoidally varying light source; and
  wherein at least one of the one or more auditory stimuli includes an amplitude modulated audio frequency.

Clause 28. The system of any preceding clause, wherein the sensory stimulus includes two or more sensory stimuli patterns, wherein at least one of the two or more sensory stimuli patterns includes a first stimuli pattern including a first pulse frequency and a second stimuli pattern including a second pulse frequency.

Clause 29. The system of any preceding clause, wherein at least one of the first pulse frequency and the second pulse frequency is between approximately 0.25 Hz and 0.75 Hz, 1.25 Hz and 1.75 Hz, 2 Hz and 4 Hz, 3.75 Hz and 4.25 Hz, or 6 Hz and 9 Hz.

Clause 30. The system of any preceding clause, wherein the first pulse frequency is between approximately 0.25 Hz and 0.75 Hz, 1.25 Hz and 1.75 Hz, 3.75 Hz and 4.25 Hz, 2 Hz and 4 Hz, or 6 Hz and 9 Hz; and
  wherein the second pulse frequency is between approximately 0.25 Hz and 0.75 Hz, 1.25 Hz and 1.75 Hz, 2 Hz and 4 Hz, 3.75 Hz and 4.25 Hz, or 6 Hz and 9 Hz.

No part of the description in this application should be read as implying that any particular element, step, or function is an essential element that must be included in the claim scope. The scope of patented subject matter is defined only by the claims. Moreover, none of the claims is intended to invoke 25 U.S.C. § 104(f) unless the exact words "means for" are followed by a participle.

The foregoing description, for purposes of explanation, use specific nomenclature to provide a thorough understanding of the described embodiments. However, it should be apparent to one skilled in the art that the specific details are not required to practice the described embodiments. Thus, the foregoing descriptions of specific embodiments are presented for purposes of illustration and description. They are not intended to be exhaustive or to limit the described embodiments to the precise forms disclosed. It should be apparent to one of ordinary skill in the art that many modifications and variations are possible in view of the above teachings.

The above discussion is meant to be illustrative of the principles and various embodiments of the present disclosure. Once the above disclosure is fully appreciated, numerous variations and modifications will become apparent to those skilled in the art. It is intended that the following claims be interpreted to embrace all such variations and modifications.

What is claimed is:

1. A method of treating fibromyalgia, comprising:
  administering a therapeutically effective amount of a sensory stimulus to a person, wherein the sensory stimulus includes one or more visual stimuli and one or more auditory stimuli,
  wherein the sensory stimulus alternates between:
  a first sensory stimuli including simultaneously providing a left visual stimuli pattern to a left eye of the person and a right auditory stimuli pattern to a right side of a head of the person, and
  a second sensory stimuli including simultaneously providing a right visual stimuli pattern to a right eye of the person and a left auditory stimuli pattern to a left side of the head of the person,
  wherein the left auditory stimuli pattern or the right auditory stimuli pattern comprises a sequence of stimuli patterns including a first stimuli pattern having a first pulse frequency, a second stimuli pattern having a second pulse frequency, and a third stimuli pattern having a third pulse frequency,
  wherein the left visual stimuli pattern comprises a pulse of a light source at a first carrier light wavelength and the right visual stimuli pattern comprises the pulse of the light source at a second carrier light wavelength;
  obtaining a measurement of the person using a sensor;
  determining a state of the person from the measurement, the state of the person comprising a state of sleep or a level or a change in a level of calmness or a level of arousal;
  modifying the sensory stimulus according to the state of the person; and
  wherein the first pulse frequency is at or between 7.5 Hz and 8.5 Hz, the second pulse frequency is at or between 2.5 Hz and 3.5 Hz, and the third pulse frequency is at or between 0.5 Hz and 1.5 Hz.

2. The method of claim 1, further comprising:
  treating one or more symptoms of fibromyalgia, wherein the one or more symptoms of fibromyalgia are selected from a group consisting of anxiety, pain, depression, and one or more sleep disorders.

3. The method of claim 1, wherein the first carrier light wavelength is equal to the second carrier light wavelength.

4. The method of claim 1, wherein the first carrier light wavelength is 580 nanometers.

5. The method of claim 1, further comprising:
periodically providing the sensory stimuli including simultaneously providing the left visual stimuli pattern to the left eye of the person, the right visual stimuli pattern to the right eye of the person, the left auditory stimuli pattern to the left side of the head, and the right auditory stimuli pattern to the right side of the head of the person.

6. The method of claim 1, wherein the one or more of the left auditory stimuli pattern or the right auditory stimuli pattern includes an auditory frequency of approximately 240 Hertz (Hz) to 480 Hz.

7. The method of claim 1, wherein the first sensory stimuli further includes providing a right tactile stimuli pattern to the right side of the head of the person simultaneously with the left visual stimuli pattern and the right auditory stimuli pattern, and wherein the second sensory stimuli further includes providing a left tactile stimuli pattern to the left side of the head of the person simultaneously with the right visual stimuli pattern and the left auditory stimuli pattern.

8. The method of claim 1, wherein the pulse of the light source occurs for a predetermined time interval.

9. The method of claim 8, wherein the predetermined time interval is between approximately 25 and 45 seconds.

10. The method of claim 1, wherein the sequence of stimuli patterns each include a pulse frequency including a pulse period, wherein a portion of the pulse period includes a stimulus of an auditory frequency of between approximately 240 Hertz (Hz) and 480 Hz.

11. The method of claim 10, wherein the portion of the pulse period is one half of the pulse period.

12. A system for treating fibromyalgia, comprising:
a headset configured to be worn on a head of a person, the headset comprising a sensor, a frame, a left light source, a left auditory source, a right light source, and a right auditory source;
a processor communicatively coupled to the headset and a controller, wherein the processor is configured to receive a sensory stimuli from the controller and transmit the sensory stimuli to the headset, wherein the sensory stimuli is transmitted at a therapeutically effective amount and the sensory stimuli alternates between:
a first sensory stimuli including simultaneously providing a left visual stimuli pattern to a left eye of the person and a right auditory stimuli pattern to a right side of the head of the person, and
a second sensory stimuli including simultaneously providing a right visual stimuli pattern to a right eye of the person and a left auditory stimuli pattern to a left side of the head of the person,
wherein the left auditory stimuli pattern or the right auditory stimuli pattern comprises a sequence of stimuli patterns including a first stimuli pattern having a first pulse frequency, a second stimuli pattern having a second pulse frequency, and a third stimuli pattern having a third pulse frequency, and
wherein the processor is further configured to obtain a measurement of the person using the sensor, determine a state of the person from the measurement, modify the sensory stimuli according to the state of the person, the state of the person comprising a state of sleep or a level or a change in a level of calmness or a level of arousal; and
wherein the first pulse frequency is at or between 7.5 Hz and 8.5 Hz, the second pulse frequency is at or between 2.5 Hz and 3.5 Hz, and the third pulse frequency is at or between 0.5 Hz and 1.5 Hz.

13. A headset for administering treatment for fibromyalgia to a person, comprising:
a frame configured to be worn on a head of the person;
a sensor;
a processor configured to generate a plurality of inputs including a left light source input, a right light source input, a left auditory source input, and a right auditory source input;
a left light source configured to produce, using the left light source input, a left visual stimuli pattern;
a right light source configured to produce, using the right light source input, a right visual stimuli pattern;
a left auditory source configured to produce, using the left auditory source input, a left auditory stimuli pattern; and
a right auditory source configured to produce, using the right auditory source input, a right auditory stimuli pattern,
wherein the processor is further configured to administer, via the headset, a therapeutically effective amount of the treatment to the person, wherein the plurality of inputs alternate between:
a first input including simultaneously generating the left light source input and the right auditory source input, and
a second input including simultaneously generating the right light source input and the left auditory source input,
wherein the first input and the second input include a first stimulus pattern having a first pulse frequency, a second stimulus pattern having a second pulse frequency, and a third stimulus pattern having a third pulse frequency;
wherein the processor is further configured to obtain a measurement of the person using the sensor, determine a state of the person from the measurement, modify the sensory stimuli according to the state of the person, the state of the person comprising a state of sleep or a level or a change in a level of calmness or a level of arousal; and
wherein the first pulse frequency is at or between 7.5 Hz and 8.5 Hz, the second pulse frequency is at or between 2.5 Hz and 3.5 Hz, and the third pulse frequency is at or between 0.5 Hz and 1.5 Hz.

* * * * *